United States Patent
Crow et al.

(10) Patent No.: US 11,702,668 B2
(45) Date of Patent: Jul. 18, 2023

(54) PLANT REGULATORY ELEMENTS AND METHODS OF USE THEREOF

(71) Applicant: PIONEER HI-BRED INTERNATIONAL, INC., Johnston, IA (US)

(72) Inventors: Andrew Carl Crow, Grimes, IA (US); Scott Diehn, West Des Moines, IA (US); Lynne Eileen Sims, Polk City, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/056,219

(22) PCT Filed: May 20, 2019

(86) PCT No.: PCT/US2019/033040
§ 371 (c)(1),
(2) Date: Nov. 17, 2020

(87) PCT Pub. No.: WO2019/226508
PCT Pub. Date: Nov. 28, 2019

(65) Prior Publication Data
US 2021/0230622 A1 Jul. 29, 2021

Related U.S. Application Data

(60) Provisional application No. 62/674,994, filed on May 22, 2018.

(51) Int. Cl.
*C12N 15/82* (2006.01)

(52) U.S. Cl.
CPC ....... *C12N 15/8223* (2013.01); *C12N 15/823* (2013.01); *C12N 15/8286* (2013.01)

(58) Field of Classification Search
None
See application file for complete search history.

(56) References Cited

FOREIGN PATENT DOCUMENTS

WO 2013/038294 A1 3/2013
WO 2017/222821 A2 12/2017

OTHER PUBLICATIONS

Kim et al, Plant Mol Biol 24: 105-117, 1994 (Year: 1994).*
Coussens, Griet; et al.: "Brachypodium distachyon promoters as efficient building blocks for transgenic research in maize", Journal of Experimental Botany, Apr. 20, 2012 (Apr. 20, 2012), vol. 63, No. 11, pp. 4263-4273.
Database GenBank NCBI Reference Sequence: NC_016134.3: "Brachypodium distachyon strain Bd21 chromosome 4, Brachypodium_distachyon_v3.0, whole genome shotgun sequence," Mar. 27, 2018 (Mar. 27, 2018). Accession No. XP002792926.
Database GenBank NCBI Reference Sequence: NW_019841141.1: "Brachypodium distachyon strain Bd21 chromosome 4 genomic scaffold, Brachypodium_distachyon_v3.0, whole genome shotgun sequence," Mar. 27, 2018 (Mar. 27, 2018). Accession No. XP002792927.
International Brachypodium Initiative: "Genome Sequencing and analysis of the model grass *Brachypodium distachyon*", Nature, Feb. 1, 2010 (Feb. 1, 2010)vol. 463, No. 7282, pp. 763-768.
Database NCBI Reference Sequence: XP_00891402.1: "Predicted: methanol O-anthraniloyltransferase-like [Malus domestica]," Mar. 27, 2018 (Mar. 27, 2018). Accession No. XP002792928.
International Search Report and Written Opinion for International Application No. PCT/US2019/033040, dated Jul. 30, 2019.

* cited by examiner

*Primary Examiner* — Medina A Ibrahim

(57) ABSTRACT

The present disclosure relates to the field of plant molecular biology, more particularly to regulation of gene expression in plants.

17 Claims, 1 Drawing Sheet

Specification includes a Sequence Listing.

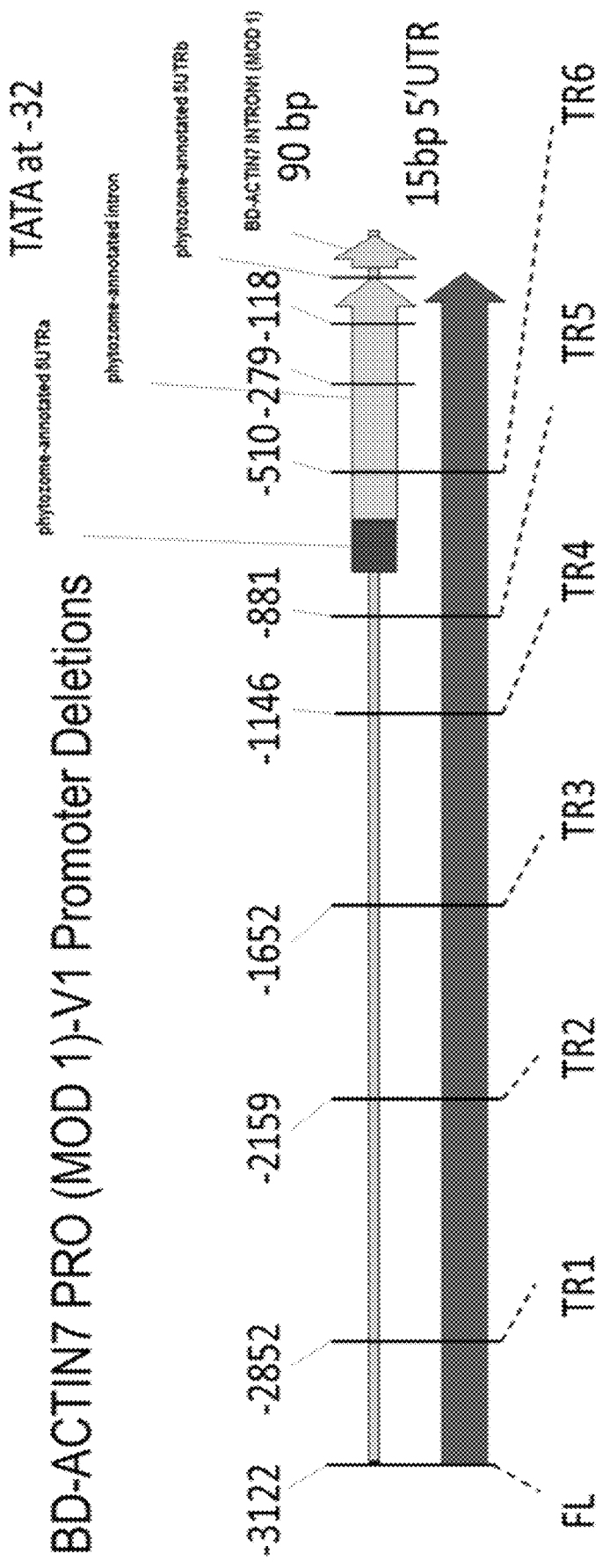

PLANT REGULATORY ELEMENTS AND METHODS OF USE THEREOF

CROSS-REFERENCE TO RELATED APPLICATIONS

This application claims the benefit of U.S. Provisional Application No. 62/674,994, filed May 5, 2018, which is hereby incorporated herein in its entirety by reference.

REFERENCE TO SEQUENCE LISTING SUBMITTED ELECTRONICALLY

A sequence listing having the file name "7439WO_SeqList.txt" created on May 18, 2019, and having a size of 25 kilobytes is filed in computer readable form concurrently with the specification. The sequence listing is part of the specification and is herein incorporated by reference in its entirety.

FIELD

The present disclosure relates to the field of plant molecular biology, more particularly to the regulation of gene expression in plants.

BACKGROUND

Expression of heterologous DNA sequences in a plant host is dependent upon the presence of operably linked regulatory elements that are functional within the plant host. Choice of promoter sequence may determine when and where within the organism a heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Genetically altering plants through the use of genetic engineering techniques and thus producing a plant with useful traits may require the availability of a variety of regulatory elements. An accumulation of promoters and other regulatory elements would enable the investigator to express at desired levels and cellular locales recombinant DNA molecules. Therefore, a collection of promoters would allow for a new trait to be expressed at the desired level in the desired tissue. Thus, isolation, characterization, and creation of regulatory elements that may produce an expression pattern that is unique and serve as regulatory regions for expression of heterologous nucleotide sequences of interest are useful for the genetic manipulation of plants.

SUMMARY

Compositions and methods for regulating expression of a heterologous polynucleotide sequence of interest in a plant or plant cell are provided. DNA molecules comprising novel polynucleotide sequences for regulatory elements that initiate transcription are provided. In some embodiments the regulatory element has promoter activity initiating transcription in a plant cell. Certain embodiments comprise the nucleotide sequences set forth in SEQ ID NOs: 1-12. Also included are functional fragments, segments, or variants of the sequences set forth in SEQ ID NOs: 1-12 wherein said sequences initiate transcription in a plant cell, or a polynucleotide sequence comprising a sequence having at least 85% sequence identity to any one of the sequences set forth in SEQ ID NOs: 1-12, wherein said sequences initiate transcription in the plant cell. Embodiments also include DNA constructs comprising a promoter operably linked to a heterologous nucleotide sequence of interest, wherein said promoter is capable of driving expression of said heterologous nucleotide sequence in a plant cell and said promoter comprises one of the nucleotide sequences disclosed herein. Embodiments also include DNA constructs comprising an enhancer and a heterologous promoter operably linked to a heterologous polynucleotide sequence of interest, wherein said enhancer and heterologous promoter are capable of driving expression of said polynucleotide sequence in a plant cell and said heterologous promoter comprises one of the polynucleotide sequences set forth in SEQ ID NOs: 1-12. Embodiments further provide expression vectors, and plants or plant cells having stably incorporated into their genomes a DNA construct as is described above. Additionally, compositions include transgenic seed of such plants.

Embodiments also include DNA constructs comprising a *Brachypodium distachyon* Actin7 (Bd-Actin7) promoter operably linked to a heterologous polynucleotide sequence of interest, wherein said promoter is capable of driving expression of said heterologous polynucleotide sequence in a plant cell and said promoter comprises one of SEQ ID NOs: 1-12, or a functional fragment thereof, as disclosed herein. Embodiments further provide expression vectors, and plants or plant cells having stably incorporated into their genomes a DNA construct as is described above. Additionally, compositions include transgenic seed of such plants.

Downstream from the transcriptional initiation region of the regulatory element will be a sequence of interest that will provide for modification of the phenotype of the plant. Such modification includes modulating the production of an endogenous product as to amount, relative distribution, or the like, or production of an exogenous expression product, to provide for a novel or modulated function or product in the plant. For example, a heterologous polynucleotide sequence that encodes a gene product that confers resistance or tolerance to herbicide, salt, cold, drought, pathogen, nematodes or insects is encompassed.

In a further embodiment, a method for modulating expression of a gene in a stably transformed plant is provided, comprising the steps of (a) transforming a plant cell with a DNA construct comprising a regulatory element disclosed herein, or a functional fragment thereof, operably linked to at least one heterologous polynucleotide sequence; (b) growing the plant cell under plant growing conditions and (c) regenerating a stably transformed plant from the plant cell wherein expression of the linked nucleotide sequence alters the phenotype of the plant. In another embodiment, the DNA construct further comprises a heterologous enhancer element.

Expression cassettes comprising the regulatory element sequences of SEQ ID NOs: 1-12 operably linked to a heterologous polynucleotide sequence of interest are provided. Additionally provided are transformed plant cells, plant tissues, seeds, and plants comprising said expression cassettes.

DESCRIPTION OF FIGURES

FIG. 1 shows the structure of the full length (3122 bp) Bd-Actin7 regulatory region and truncations of the regulatory region. The regulatory region was truncated (TR) from the 5' end to segments that comprised 2852 bp (SEQ ID NO: 5), 2174 bp (SEQ ID NO: 6), 1666 bp (SEQ ID NO: 7), 1161 bp (SEQ ID NO: 8), 907 bp (SEQ ID NO: 9), and 528 bp (SEQ ID NO: 10).

DESCRIPTION OF SEQUENCES

TABLE 1

Sequence Listing Description

| SEQ ID NO | Sequence name |
|---|---|
| 1 | BD-ACTIN7 PRO (MOD1) |
| 2 | BD-ACTIN7 PRO (Phytozome annotation) |
| 3 | BD-ACTIN7 INTRON in PRO (Phytozome annotation) |
| 4 | BD-ACTIN7 INTRON1 (MOD1) |
| 5 | BD-ACTIN7 PRO (MOD1) (TR1) |
| 6 | BD-ACTIN7 PRO (MOD1) (TR2) |
| 7 | BD-ACTIN7 PRO (MOD1) (TR3) |
| 8 | BD-ACTIN7 PRO (MOD1) (TR4) |
| 9 | BD-ACTIN7 PRO (MOD1) (TR5) |
| 10 | BD-ACTIN7 PRO (MOD1) (TR6) |
| 11 | BD-ACTIN7 PRO (MOD1) (TR7) |
| 12 | BD-ACTIN7 PRO (MOD1) (TR8) |
| 13 | 3xMMV Enhancer |
| 14 | Zm-HPLV9 intron1 |
| 15 | Zm-HPSV11 intron1 |
| 16 | ADH intron1 |

DETAILED DESCRIPTION

The article "a" and "an" are used herein to refer to one or more than one (i.e., to at least one) of the grammatical object of the article. By way of example, "an element" means one or more element.

The disclosure relates to compositions and methods drawn to plant regulatory elements and methods of their use. The compositions comprise nucleotide sequences for the regulatory region of *Brachypodium distachyon* Actin7 (Bd-Actin7). The compositions further comprise DNA constructs comprising at least one polynucleotide sequence for the regulatory region of the Bd-Actin7 promoter operably linked to a heterologous polynucleotide sequence of interest. In particular, isolated nucleic acid molecules comprising the polynucleotide sequences set forth in SEQ ID NOs: 1-13, and fragments, variants and complements thereof are provided.

The regulatory element sequences, SEQ ID NOs: 1-13, include polynucleotide constructs that allow initiation of transcription in a plant. In specific embodiments, a regulatory element allows initiation of transcription in a constitutive manner. Such constructs may comprise regulated transcription initiation regions associated with plant developmental regulation. Thus, the compositions disclosed herein may include DNA constructs comprising a nucleotide sequence of interest operably linked to a plant promoter, particularly a constitutive promoter sequence, more particularly a promoter and intron sequence. In another preferred embodiment, the DNA construct further comprises a heterologous enhancer element. In one embodiment, a heterologous enhancer element comprises SEQ ID NOs: 13.

The nucleotide sequences may also find use in the construction of expression vectors for subsequent expression of a heterologous nucleotide sequence in a plant of interest or as probes for the isolation of other regulatory elements. One embodiment is provided for DNA constructs comprising a regulatory element polynucleotide sequence set forth in SEQ ID NOs: 1-13, or a functional fragment or variants thereof, operably linked to a heterologous polynucleotide sequence of interest, and any combinations thereof.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

Regulatory elements such as promoters, enhancers, leaders, and intron regions are nucleic acid molecules that have gene regulatory activity and play an integral part in the overall expression of genes in living cells. Isolated regulatory elements, such as promoters and leaders that function in plants are therefore useful for modifying plant phenotypes through the methods of genetic engineering. A promoter is useful as a regulatory element for modulating the expression of an operably linked transcribable polynucleotide molecule.

As used herein, a "gene expression pattern" is any pattern of transcription of an operably linked nucleic acid molecule into a transcribed RNA molecule. Expression may be characterized by its temporal, spatial, developmental, tissue, environmental, physiological, pathological, cell cycle, and/ or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

The regulatory element sequences or variants or fragments thereof, when operably linked to a heterologous polynucleotide sequence of interest may drive constitutive expression of the heterologous polynucleotide sequence in the tissue of the plant expressing this construct. The term "constitutive expression," means that expression of the heterologous nucleotide sequence is found throughout the plant or in a majority of tissues of the plant.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a nucleic acid molecule that is involved in recognition and binding of RNA polymerase II and other proteins (trans-acting transcription factors) to initiate transcription. A promoter may be initially isolated from the 5' flanking region of a genomic copy of a gene. Alternately, promoters may be synthetically produced or manipulated DNA molecules. Regulatory elements may comprise promoters and promoter activity. As used herein, "promoter activity" refers to the ability of a regulatory element to initiate transcription. Promoter activity may occur in vivo, such as in a cell, or in vitro.

In one embodiment, fragments are provided of a regulatory element disclosed herein. Regulatory element fragments may exhibit promoter activity, and may be useful alone or in combination with other regulatory elements and regulatory element fragments, such as in constructing hybrid regulatory elements (See International Patent Publication Number WO 2017/222821). In specific embodiments, fragments of a regulatory element are provided comprising, or alternatively consisting of or consisting essentially of, at least about 50, 95, 150, 250, 500, or about 750 or more contiguous nucleotides of a polynucleotide molecule having promoter activity disclosed herein. Such fragments may exhibit at least about 85 percent, about 90 percent, about 95 percent, about 98 percent, or about 99 percent, or greater, identity with a reference sequence disclosed herein when optimally aligned to the reference sequence. As used herein, the term "regulatory element segment" is a fragment of a regulatory element characterized by an abundance of recognizable regulatory element motifs (See Higo, K et al. (1998) Nucleic Acids Research), wherein the regulatory element segment produces a desired or unique expression pattern when combined with at least two other regulatory element segments.

A regulatory element or a regulatory element segment may also be analyzed for the presence of known promoter motifs, i.e. DNA sequence characteristics, such as a TATA-box and other known transcription factor binding site motifs. Identification of such known motifs may be used by one of skill in the art to design hybrid regulatory elements having a desired or unique expression pattern when compared to the source or parent regulatory element. Nucleotide sequence motifs found in regulatory elements have been previously characterized and many are available in the PLACE database (Higo, K et al. (1998) Nucleic Acids Research; dna.af-frc.go.jp/htdocs/PLACE/, which can be accessed on the world-wide web using the "www" prefix; See also, PCT Application Number WO 2014/164399). In some embodiments, a regulatory element segment comprises about 15, 20, 25, 30, 35, 40, 45, 50, 75, 100, 125, 150, 175, or 200 motifs per 1000 nucleotides. In some embodiments, a regulatory element comprises at least one motif for about every 5, 10, 15, 20, 25, 30, 35, 40, 45, or 50 nucleotides. In one embodiment, a hybrid regulatory element comprises a segment, fragment, or variant of SEQ ID NOs: 1-13, wherein the segment, fragment, or variant of SEQ ID NOs: 1-13 comprises about 15, 20, 25, 30, 35, 40, 45, 50, 75, 100, 125, 150, 175, or 200 motifs per 1000 nucleotides.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A regulatory element may naturally comprise one or more enhancer elements that affect the transcription of an operably linked polynucleotide sequence. An isolated enhancer element may also be fused to a heterologous promoter to produce a heterologous promoter cis-element, which confers an aspect of the overall modulation of gene expression. A regulatory element or regulatory element fragment disclosed herein may comprise one or more enhancer elements that effect the transcription of operably linked genes. Many enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain Enhancer elements may be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain may be further studied by mutagenesis (or substitution) of one or more nucleotides or by other conventional methods Enhancer elements may be obtained by chemical synthesis or by isolation from regulatory elements that include such elements, and they may be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed.

As used herein, the term "5' flanking region" refers to a DNA molecule isolated from a genomic copy of a gene and is defined generally as a polynucleotide segment beginning at the protein coding sequence start site and extending 5' through the 5' untranslated region and into the promoter region. These sequences, or leaders, may be synthetically produced or manipulated DNA elements. A leader may be used as a 5' regulatory element for modulating expression of an operably linked transcribable polynucleotide molecule. Leader molecules may be used with heterologous elements or with their native elements.

As used herein, the term "hybrid" refers to a single synthetic DNA molecule produced by fusing a first DNA molecule to a second DNA molecule, where neither first nor second DNA molecule would normally be found in that configuration, i.e. fused to the other. The hybrid DNA molecule is thus a new DNA molecule not normally found in nature. As used herein, the term "hybrid regulatory element" refers to a regulatory element produced through such manipulation of DNA molecules. A hybrid regulatory element may combine three or more DNA fragments. Thus, the design, construction, and use of hybrid regulatory element according to the methods disclosed herein for modulating the expression of operably linked transcribable polynucleotide molecules are encompassed. In one embodiment, a hybrid regulatory element comprises three or more DNA defined segments. In another embodiment, a hybrid regulatory element comprises 4 or more DNA fragments. In one embodiment, a DNA fragment may be a parent fragment. As used herein, a "segment," and "parent segment" are interchangeable and intended to refer to fragments of native "parent regulatory elements" that have been analyzed for motifs that are predicted to produce a regional tissue expression pattern. A combination of parent segments or variants thereof, may result in a hybrid regulatory element expressing a gene of interest in a ubiquitous tissue expression pattern that is unique from each individual expression pattern of the parent regulatory elements. In one embodiment, a parent segment may be a variant of a parent regulatory element. In one embodiment, parent regulatory elements set forth in SEQ ID NOs: 1-13 may be used as parent regulatory elements to generate parent segments and variants thereof. Also, included as parent regulatory elements are functional fragments, segments, or variants of the polynucleotide sequences set forth in SEQ ID NOs: 1-13 wherein said polynucleotide sequences initiate transcription in a plant cell, and a polynucleotide sequence comprising a sequence having at least 85% sequence identity to the polynucleotide sequences set forth in SEQ ID NOs: 1-13, wherein said polynucleotide sequences initiate transcription in a plant cell.

Hybrid regulatory elements are provided that produce an expression pattern in plants that is unique relative to parent regulatory elements, wherein the hybrid regulatory element contains segments or fragments of more than one parent regulatory element. In one embodiment, the hybrid regulatory element produces a tissue specific expression pattern that is different relative to the regulatory elements. In another embodiment, the hybrid regulatory elements broaden the expression pattern to a ubiquitous expression pattern in a plant tissue relative to regional tissue expression patterns expressed from a given set of parent regulatory elements. In another embodiment, the hybrid regulatory elements express a narrower range of expression relative to a broader range of expression patterns expressed from a given set of parent regulatory elements. In another embodiment, the hybrid root regulatory elements may produce a constitutive expression pattern that differs from a non-constitutive expression pattern of the parent regulatory elements.

In one embodiment, the polynucleotide sequences disclosed herein, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. A post-transcriptional regulatory element may include elements that are active following transcription initiation, for example translational and transcriptional enhancers, translational and transcriptional repressors, and mRNA stability determinants.

The regulatory elements, or variants or fragments thereof, may be operatively associated with one or more heterologous regulatory elements in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements, or fragments thereof, may be operatively associated with constitutive, inducible, or tissue specific promoters or fragment thereof, to modulate the activity of such promoters within desired tissues in plant cells.

The compositions may encompass isolated or recombinant nucleic acid. An "isolated" or "recombinant" nucleic acid molecule (or DNA) is used herein to refer to a nucleic acid sequence (or DNA) that is no longer in its natural environment, for example in an in vitro or in a heterologous recombinant bacterial or plant host cell. An isolated or recombinant nucleic acid molecule, or biologically active portion thereof, is substantially free of other cellular material or culture medium when produced by recombinant techniques, or substantially free of chemical precursors or other chemicals when chemically synthesized. An isolated or recombinant nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule may contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The regulatory element sequences disclosed herein may be isolated from the 5' untranslated region flanking their respective transcription initiation sites. As used herein, the terms "polynucleotide" and "nucleotide" are both intended to mean one or more nucleotide and may be used interchangeably in the singular or plural.

Fragments and variants of the disclosed regulatory element polynucleotide sequences are also encompassed by the present disclosure. As used herein, the term "fragment" refers to a portion of the nucleic acid sequence. Fragments of regulatory sequences may retain the biological activity of initiating transcription, more particularly driving transcription in a tissue specific or sub-tissue specific manner. Alternatively, fragments of a polynucleotide sequence that are useful as hybridization probes may not necessarily retain biological activity. Fragments of a polynucleotide sequence for the regulatory region may range from at least about 20 nucleotides, about 50 nucleotides, about 100 nucleotides, and up to the full length of SEQ ID NOs: 1-13.

A biologically active portion of a regulatory element may be prepared by isolating a portion of the regulatory sequence, and assessing the promoter activity of the portion. Nucleic acid molecules that are fragments of a regulatory polynucleotide sequence comprise at least about 16, 50, 75, 100, 150, 200, 250, 300, 350, 400, 450, 500, 550, 600, 650, 700 or 800 nucleotides or up to the number of nucleotides present in a full-length regulatory sequence disclosed herein.

For polynucleotide sequences, a variant comprises a deletion and/or addition of one or more nucleotides at one or more internal sites within the native polynucleotide sequence and/or a substitution of one or more nucleotides at one or more sites in the native polynucleotide. For polynucleotide sequences, variants may be identified with the use of well-known molecular biology techniques, as, for example, with polymerase chain reaction (PCR) and hybridization techniques as outlined below. Variant polynucleotide sequences may include synthetically derived polynucleotide sequences, such as those generated, for example, by using site-directed mutagenesis. Generally, variants of a particular nucleotide sequence of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a polynucleotide sequence of the disclosure may differ from that sequence by as few as 1-15 nucleic acid residues, as few as 1-10, as few as 6-10, as few as 5, as few as 4, 3, 2, or even 1 nucleic acid residue.

Variant polynucleotide sequences also encompass sequences derived from a mutagenic and recombinogenic procedure such as DNA shuffling. With such a procedure, regulatory element polynucleotide sequences may be manipulated to create new regulatory elements. In this manner, libraries of recombinant polynucleotides are generated from a population of related sequence polynucleotides comprising sequence regions that have substantial sequence identity and may be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The polynucleotide sequences of the disclosure may be used to isolate corresponding sequences from other organisms, particularly other plants, more particularly other monocots. In this manner, methods such as PCR, hybridization and the like may be used to identify such sequences based on their sequence homology to the sequences set forth herein. Sequences isolated based on their sequence identity to the entire sequences set forth herein or to fragments thereof are encompassed by the present disclosure.

In a PCR approach, oligonucleotide primers may be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide sequence is used as a probe that selectively hybridizes to other corresponding polynucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as $^{32}P$ or any other detectable marker. Thus, for example, probes for hybridization may be made by labeling synthetic oligonucleotides based on the regulatory element sequences of the disclosure. Methods for preparation of probes for hybridization and for construction of genomic libraries are generally known in the art and are disclosed in Sambrook, supra.

For example, an entire regulatory element sequence disclosed herein, or one or more portions thereof, may be used as a probe capable of specifically hybridizing to corresponding regulatory element sequences and messenger RNAs. To achieve specific hybridization under a variety of conditions, such probes include sequences that are unique among regulatory element sequences and are generally at least about 10 nucleotides in length or at least about 20 nucleotides in length. Such probes may be used to amplify corresponding regulatory element sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies, see, for example, Sambrook, supra).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions may be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1 times to 2 times SSC (20 times SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5 times to 1 times SSC at 55 to 60° C. Exemplary high stringency conditions include hybridization in 50% formamide, 1 M NaCl, 1% SDS at 37° C., and a final wash in 0.1 times SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, (1984) Anal. Biochem 138:267 284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology—Hybridization with Nucleic Acid Probes, Part I, Chapter 2 (Elsevier, New York); and Ausubel, et al., eds. (1995) Current Protocols in Molecular Biology, Chapter 2 (Greene Publishing and Wiley-Interscience, New York), herein incorporated by reference in their entirety. See also, Sambrook.

Thus, isolated sequences that have promoter activity and which hybridize under stringent conditions to the regulatory sequences disclosed herein or to fragments thereof, are encompassed by the present disclosure.

In general, sequences that have promoter activity and hybridize to the polynucleotide sequences, and fragments thereof, disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Another indication that polynucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein.

Modifications of the isolated regulatory element sequences of the present disclosure may provide for a range of expression of the heterologous polynucleotide sequence. Thus, they may be modified to be weak promoters or strong promoters. Generally, a "weak promoter" means a promoter that drives expression of a coding sequence at a low level. A "low level" of expression is intended to mean expression at levels of about $\frac{1}{10,000}$ transcripts to about $\frac{1}{100,000}$ transcripts to about $\frac{1}{500,000}$ transcripts. Conversely, a strong promoter drives expression of a coding sequence at a high level, or at about $\frac{1}{10}$ transcripts to about $\frac{1}{100}$ transcripts to about $\frac{1}{1,000}$ transcripts.

The regulatory elements disclosed herein may be used to increase or decrease expression, thereby resulting in a change in phenotype of the transformed plant. The polynucleotide sequences disclosed herein, as well as variants and fragments thereof, are useful in the genetic manipulation of any plant. The regulatory element sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the regulatory element sequence. In this manner, the regulatory element sequences disclosed herein may be provided in expression cassettes along with heterologous polynucleotide sequences of interest for expression in the plant of interest, more particularly for expression in the reproductive tissue of the transformed plant.

The regulatory elements of the embodiments may be provided in DNA constructs for expression in the organism of interest. An "expression cassette" as used herein means a DNA construct comprising a regulatory element of the embodiments operably linked to a heterologous polynucleotide expressing a transcript or gene of interest. Such expression cassettes will comprise a transcriptional initiation region comprising one of the regulatory element polynucleotide sequences of the present disclosure, or variants or fragments thereof, operably linked to the heterologous nucleotide sequence. Such an expression cassette may be provided with a plurality of restriction sites for insertion of the polynucleotide sequence to be under the transcriptional regulation of the regulatory regions. The expression cassette may additionally contain selectable marker genes as well as 3' termination regions.

The expression cassette may include, in the 5'-3' direction of transcription, a transcriptional initiation region (i.e., a hybrid promoter, or variant or fragment thereof, of the disclosure), a translational initiation region, a heterologous polynucleotide sequence of interest, a translational termination region and optionally, a transcriptional termination region functional in the host organism. The regulatory regions (i.e., promoters, enhancers, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other.

As used herein, "heterologous" in reference to a sequence is a sequence that originates from a foreign species or, if from the same species, is substantially modified from its native form in composition and/or genomic locus by deliberate human intervention. For example, a regulatory element operably linked to a heterologous polynucleotide is from a species different from the species from which the polynucleotide was derived or, if from the same/analogous species, one or both are substantially modified from their original form and/or genomic locus or the regulatory element is not the native regulatory element for the operably linked polynucleotide.

The termination region may be native with the transcriptional initiation region, may be native with the operably linked DNA sequence of interest, may be native with the plant host, or may be derived from another source (i.e., foreign or heterologous to the regulatory element, the DNA sequence being expressed, the plant host, or any combination thereof).

The regulatory elements disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of heterologous nucleic acid, including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant and selection of a particular plant characterized by insertion into a particular genome location. An event is characterized phenotypically by the expression of the transgene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the disclosure, provided that these parts comprise the introduced polynucleotides.

The compositions and methods disclosed herein may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed include, for example, pines such as loblolly pine (*Pinus taeda*), slash pine (*Pinus elliotii*), ponderosa pine (*Pinusponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of may be crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by a regulatory element sequence disclosed herein may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought and the like. These results may be achieved by the expression of a heterologous polynucleotide sequence of interest comprising an appropriate gene product. In specific embodiments, the heterologous polynucleotide sequence of interest is an endogenous plant sequence whose expression level is increased in the plant or plant part. Results may be achieved by providing for altered expression of one or more endogenous gene products, particularly hormones, receptors, signaling molecules, enzymes, transporters or cofactors or by affecting nutrient uptake in the plant. These changes result in a change in phenotype of the transformed plant. In certain embodiments the expression patterns of the regulatory elements disclosed herein are useful for many types of screening.

General categories of polynucleotide sequences of interest that may be utilized with the regulatory sequences disclosed herein include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc) and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the regulatory element of the disclosure and expressed in the plant.

By way of illustration, without intending to be limiting, the following is a list of other examples of the types of genes which may be used in connection with the regulatory elements disclosed herein.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of U.S. Ser. No. 13/792,861; an AfIP-1A and/or AfIP-1B polypeptide of U.S. Ser. No. 13/800,233; a PHI-4 polypeptide of U.S. Ser. No. 13/839, 702; a PIP-47 polypeptide of PCT Serial Number PCT/US14/51063; a PIP-72 polypeptide of PCT Serial Number PCT/US14/55128; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #126149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #112419); Cry1Ab12

(Accession #AAC64003); Cry1Ab13 (Accession #AAN76494); Cry1Ab14 (Accession #AAG16877); Cry1Ab15 (Accession #AA013302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AA039719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AA039720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #I76415); Cry1Da3 (Accession #HQ439784); Cry1db1 (Accession #CAA80234); Cry1db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #IQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AA013295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AA013756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession

HM439636); Cry11e3 (Accession #KC156647); Cry11e4 (Accession #KC156681); Cry11f1 (Accession #AAQ52382); Cry11g1 (Accession #KC156701); Cry11-like (Accession #AAC31094); Cry11-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AAO13750); Cry2Aa10 (Accession #AAQ04263); Cry2Aa11 (Accession #AAQ52384); Cry2Aa12 (Accession #AB183671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #F1788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #J9397327); Cry3Bb1 (Accession #AAA22334); Cry3Bb2 (Accession #AAA74198); Cry3Bb3 (Accession #115475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #I34543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2

(Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #I32932); Cry21Aa2 (Accession #I66477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #I34547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32o1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession

BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EA057254); Cry60Aa3 (Accession #EEM99278); Cry60Ba1 (Accession #GU810818); Cry60Ba2 (Accession #EA057253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC3131, TIC 3400, and TIC3407 of US Patent Application Publication Number 2015/0047076; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) 1 Invert. Path. 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605)); Cry34Ab/35Ab and Cry6Aa (US20130167269); Cry34Ab/VCry35Ab & Cry3Aa (US20130167268); Cry3A and Cry1Ab or Vip3Aa (US20130116170); and Cry1F, Cry34Ab1, and Cry35Ab1 (PCT/US2010/060818). Pesticidal proteins also include insecticidal lipases including lipid acyl hydrolases of U.S. Pat. No. 7,491,869, and cholesterol oxidases such as from *Streptomyces* (Purcell et al. (1993) Biochem Biophys Res Commun 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(D) An insect-specific peptide which, upon expression, disrupts the physiology of the affected pest. For example, see the disclosures of Regan, (1994) *J Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4): 385-403. See also, U.S. Pat. No. 5,266,317 to Tomalski, et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ub14-2 polyubiquitin gene, U.S. patent application Ser. Nos. 10/389,432, 10/692,367 and U.S. Pat. No. 6,563,020.

(G) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes, et al., (1993) Plant Sci. 89:43, of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki, et al., (1993) Nature 366:469, who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) Bio/Technology 10:1436. The cloning and characterization of a gene which encodes a bean endopolygalacturonase-inhibiting protein is described by Toubart, et al., (1992) Plant J. 2:367.

(N) A developmental-arrestive protein produced in nature by a plant. For example, Logemann, et al., (1992) Bio/Technology 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) Current Biology 5(2):128-131, Pieterse and Van Loon, (2004) Curr. Opin. Plant Bio. 7(4):456-64 and Somssich, (2003) Cell 113(7):815-6.

(P) Antifungal genes (Cornelissen and Melchers, (1993) Pl. Physiol. 101:709-712 and Parijs, et al., (1991) Planta 183:258-264 and Bushnell, et al., (1998) Can. J. of Plant Path. 20(2):137-149. Also see, U.S. patent application Ser. No. 09/950,933.

(Q) Detoxification genes, such as for fumonisin, beauvericin, moniliformin and zearalenone and their structurally related derivatives. For example, see, U.S. Pat. No. 5,792,931.

(R) Cystatin and cysteine proteinase inhibitors. See, U.S. application Ser. No. 10/947,979.

(S) Defensin genes. See, WO03/000863 and U.S. application Ser. No. 10/178,213.

(T) Genes conferring resistance to nematodes. See, WO 03/033651 and Urwin, et. al., (1998) Planta 204:472-479, Williamson (1999) Curr Opin Plant Bio. 2(4):327-31.

(U) Genes such as rcg1 conferring resistance to Anthracnose stalk rot, which is caused by the fungus Colletotrichum graminiola. See, Jung, et al., Generation-means analysis and quantitative trait locus mapping of Anthracnose Stalk Rot genes in Maize, Theor. Appl. Genet. (1994) 89:413-418, as well as, U.S. Provisional Patent Application No. 60/675,664.

(V) Nucleic Acids that relate to down-regulation of expression of target genes in insect pest species by interfering ribonucleic acid (RNA) molecules, which control the insect pest species. PCT Publication WO 2011/025860 and WO 2014/153254 describe methods of inhibiting expression of target genes in invertebrate plant pests including Diabrotica plant pests. Furthermore, PCT Publication WO 2009/091864 describes compositions and methods for the suppression of target genes from insect pest species including pests from the Lygus genus.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988) EMBO J. 7:1241 and Miki, et al., (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824 and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and Streptomyces hygroscopicus phosphinothricin acetyl transferase (bar) genes) and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyl-transferase. See, for example, U.S. patent application Ser. Nos. 11/405,845 and 10/427,692 and PCT Application Number US01/46227. A DNA molecule encoding a mutant aroA gene can be obtained under ATCC Accession Number 39256 and the nucleotide sequence of the mutant gene is disclosed in U.S. Pat. No. 4,769,061 to Comai. EP Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Patent Numbers 0 242 246 and 0 242 236 to Leemans, et al., De Greef, et al., (1989) Bio/Technology 7:61 which describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) Theor. Appl. Genet. 83:435.

(C) A herbicide that inhibits photosynthesis, such as a triazine (psbA and gs+ genes) and a benzonitrile (nitrilase gene). Przibilla, et al., (1991) Plant Cell 3:169, describe the transformation of Chlamydomonas with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) Biochem. J. 285:173.

(D) Acetohydroxy acid synthase, which has been found to make plants that express this enzyme resistant to multiple types of herbicides, has been introduced into a variety of plants (see, e.g., Hattori, et al., (1995) Mol Gen Genet 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1): 17-23), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373; and international publication number WO 01/12825.

3. Transgenes that Confer or Contribute to an Altered Grain Characteristic, Such as:

(A) Altered fatty acids, for example, by
(1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn),
(2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, mi1ps, various lpa genes such as lpa1, lpa3, hpt or hggt. For example, see, WO 02/42424, WO 98/22604, WO 03/011015, U.S. Pat. Nos. 6,423,886, 6,197,561, 6,825,397, US Patent Application Publication Numbers 2003/0079247, 2003/0204870, WO02/057439, WO03/011015 and Rivera-Madrid, et. al., (1995) *Proc. Natl. Acad. Sci.* 92:5620-5624.

(B) Altered phosphorus content, for example, by the
(1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. Nos. 6,197,561, 6,291,224, 6,391, 348, WO2002/059324, US Patent Application Publication Number 2003/0079247, WO98/45448, WO99/55882, WO01/04147.

(C) Altered carbohydrates effected, for example, by altering a gene for an enzyme that affects the branching pattern of starch or a gene altering thioredoxin such as NTR and/or TRX (see, U.S. Pat. No. 6,531,648) and/or a gamma zein knock out or mutant such as cs27 or TUSC27 or en27 (see, U.S. Pat. No. 6,858,778 and US Patent Application Publication Numbers 2005/0160488 and 2005/0204418). See, Shiroza, et al., (1988)*J Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) 1 *Biol. Chem.* 268:22480 (site-directed mutagenesis of barley alpha-amylase gene) and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No.

5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant and thus creating a plant that is male sterile because the inducible promoter is not "on" resulting in the male fertility gene not being transcribed. Fertility is restored by inducing, or turning "on", the promoter, which in turn allows the gene conferring male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859, 341; 6,297,426; 5,478,369; 5,824,524; 5,850,014 and 6,265, 640.

5. Genes that Create a Site for Site Specific DNA Integration

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 99/25821. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983), and the R/RS system of the pSR1 plasmid (Araki, et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see WO0202776, WO2003052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see US Patent Application Publication Number 2004/0128719, US Patent Application Publication Number 2003/0166197 and WO200032761. For plant transcription factors or transcriptional regulators of abiotic stress, see, e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAD, WO99/09174 (D8 and Rht) and WO2004076638 and WO2004031349 (transcription factors).

"RNAi" refers to a series of related techniques to reduce the expression of genes (see, for example, U.S. Pat. No. 6,506,559). These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020). Such techniques rely on the use of constructs resulting in the accumulation of double stranded RNA with one strand complementary to the target gene to be silenced. The regulatory sequences disclosed herein may be used to drive expression of constructs that will result in RNA interference including microRNAs and siRNAs.

The regulatory sequences disclosed herein may be used to drive expression of constructs targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR, HP2, and PAT3. US Patent Application publication 2011/0054007 describes polynucleotide silencing elements targeting RPS10. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

The isolated regulatory element sequences disclosed herein may be modified to provide for a range of expression levels of the heterologous nucleotide sequence. Thus, less than the entire regulatory element region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of regulatory element deletions if, for example, there is a negative regulatory element (for a repressor) that is removed during the truncation process. Generally, at least about 20 nucleotides of an isolated regulatory element sequence will be used to drive expression of a polynucleotide sequence.

Convenient termination regions are available from the Ti-plasmid of *A. tumefaciens*, such as the octopine synthase and nopaline synthase termination regions. See also, Guerineau, et al., (1991) Mol. Gen. Genet. 262:141-144; Proudfoot, (1991) *Cell* 64:671-674; Sanfacon, et al., (1991) *Genes Dev.* 5: 141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639.

Expression cassettes comprising sequences disclosed herein may also contain at least one additional nucleotide sequence for a gene to be cotransformed into the organism. Alternatively, the additional sequence(s) can be provided on another expression cassette.

Where appropriate, the polynucleotide sequences whose expression is to be under the control of a regulatory element sequence of the present disclosure and any additional nucleotide sequence(s) may be optimized for increased expression in the transformed plant. That is, these nucleotide sequences can be synthesized using plant preferred codons for improved expression. See, for example, Campbell and Gowri, (1990) *Plant Physiol.* 92:1-11, for a discussion of host-preferred codon usage. Methods are available in the art for synthesizing plant-preferred genes. See, for example, Murray, et al., (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous polynucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences may act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA, pages* 237-256) and maize chlorotic mottle virus leader (MCMV) (Lommel, et al., (1991) *Virology* 81:382-385). See, also, Della-Cioppa, et al., (1987) *Plant Physiology* 84:965-968. Methods known to enhance mRNA stability may also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize AdhI intron (Kyozuka, et al., (1991) *Mol. Gen. Genet.* 228:40-48; Kyozuka, et al., (1990)*Maydica* 35:353-357) and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in expression cassettes. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO 1* 9:2517-2522; Kain, et al., (1995) *Bio Techniques* 19:650-655 and Chiu, et al., (1996) *Current Biology* 6:325-330.

Selectable marker genes for selection of transformed cells or tissues may include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO* 1 6:2513-2518).

Other genes that could serve utility in the recovery of transgenic events would include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19): 8115 and Luehrsen, et al., (1992) *Methods Enzymol.* 216: 397-414) and the maize genes encoding for anthocyanin production (Ludwig, et al., (1990) *Science* 247:449).

Expression cassette comprising a regulatory element operably linked to a polynucleotide sequence of interest may be used to transform any plant. In another embodiment, an expression cassette comprising the sequences of SEQ ID NOs: 1-13 operably linked to a polynucleotide sequence of interest may be used to transform any plant. In this manner, genetically modified plants, plant cells, plant tissue, seed, root and the like may be obtained.

Certain disclosed methods involve introducing a polynucleotide into a plant. As used herein, "introducing" is intended to mean presenting to the plant the polynucleotide in such a manner that the sequence gains access to the interior of a cell of the plant. The methods of the disclosure do not depend on a particular method for introducing a sequence into a plant, only that the polynucleotide gains access to the interior of at least one cell of the plant. Methods for introducing polynucleotide into plants are known in the art including, but not limited to, stable transformation methods, transient transformation methods and virus-mediated methods.

A "stable transformation" is a transformation in which the polynucleotide construct introduced into a plant integrates into the genome of the plant and is capable of being inherited by the progeny thereof "Transient transformation" means that a polynucleotide is introduced into the plant and does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO* 1 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) *Plant Cell Reports* 9:415-418 and Kaeppler, et al., (1992) *Theon. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., and (1996) *Nature Biotechnology* 14:745-750 (maize via *Agrobacterium tumefaciens*).

In one embodiment, DNA constructs comprising a regulatory element may be provided to a plant using a variety of transient transformation methods. In another embodiment, DNA constructs comprising the disclosed sequences SEQ ID NOs: 1-13 may be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, a polynucleotide may be introduced into plants by contacting plants with a virus or viral nucleic acids. Generally, such methods involve incorporating a polynucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855 and WO99/25853. Briefly, the polynucleotide of the disclosure can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide construct, for example, an expression cassette comprising one of SEQ ID NOs: 1-13, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polynucleotide is cultivated using methods well known to one skilled in the art.

The embodiments provide compositions for screening compounds that modulate expression within plants. The vectors, cells and plants can be used for screening candidate molecules for agonists and antagonists of the regulatory element sequences of SEQ ID NOs: 1-13. For example, a reporter gene can be operably linked to a regulatory element sequence and expressed as a transgene in a plant. Compounds to be tested are added and reporter gene expression is measured to determine the effect on promoter activity.

In one embodiment, a regulatory element, for example sequences SEQ ID NOs: 1-13 may be edited or inserted into a plant by genome editing using a CRISPR/Cas9 system.

In an aspect, the disclosed regulatory elements may be introduced into the genome of a plant using genome editing technologies, or previously introduced regulatory elements in the genome of a plant may be edited using genome editing technologies. For example, the disclosed regulatory elements may be introduced into a desired location in the genome of a plant through the use of double-stranded break technologies such as TALENs, meganucleases, zinc finger nucleases, CRISPR-Cas, and the like. For example, the disclosed regulatory elements may be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing regulatory elements of interest could be either an endogenous regulatory element or a previously introduced regulatory element.

In another aspect, where the disclosed regulatory element has previously been introduced into a genome, genome editing technologies may be used to alter or modify the introduced regulatory element sequence. Site specific modifications that can be introduced into the disclosed regulatory elements compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

The above description of various illustrated embodiments of the disclosure is not intended to be exhaustive or to limit the scope to the precise form disclosed. While specific embodiments of examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

Efforts have been made to ensure accuracy with respect to the numbers used (e.g. amounts, temperature, concentrations, etc.), but some experimental errors and deviations should be allowed for. Unless otherwise indicated, parts are parts by weight; molecular weight is average molecular weight; temperature is in degrees centigrade; and pressure is at or near atmospheric.

EXPERIMENTAL

Example 1: *Brachypodium Distachyon* Actin7 Regulatory Element Sequences

The regulatory element of SEQ ID NO: 1 was obtained through a search of a proprietary RNA-seq database consisting of the spatial expression values for the *Brachypodium distachyon* diploid inbred line, Bd21 (*Brachypodium distachyon* (L.) Beauv USDA NPGS accession PI 254867 (Bd21)). Tissue from greenhouse grown plants was sampled from each of the major organs at vegetative and reproductive developmental stages to also provide temporal expression values for those organs present at both stages (e.g. leaves/roots). Three replicates were taken for each sample, with each replicate consisting of nine plants. RNA was isolated from each of the replicates, reverse transcribed, and sequenced using Illumina DNA sequencing technology. Sequence tags were aligned with genomic sequence to identify the gene.

A comparison of expression across each of the tissues was performed to identify candidates that fit criteria of expression in leaves and roots at both vegetative and reproductive stages, as well as in the floret and inflorescence stem at reproductive stage. Several candidates were identified including one with a sequence tag aligning to the *Brachypodium distachyon* Actin7 gene.

Using the plant comparative genomics portal of the Department of Energy's Joint Genome Institute (Phytozome), the 5' flanking region for Bd-Actin7 was identified. The sequence synthesized for testing in corn consists of 3122 bp (set forth in SEQ ID NO: 1) and has a putative TATA box starting approximately 39 bp upstream of the 3' end of the sequence. A putative transcription start site, denoted by the nucleotides CA, is approximately 24 bp downstream of the putative TATA box. The entire 3122 bp sequence is referred to herein as the "Bd-Actin7 FL" (full-length) regulatory element or Bd-Actin7 FL. Deleting segments of the 5' end of the full-length regulatory element can alter the expression pattern and provide insight into important sequence markers in the regulatory region. SEQ ID NOs: 6-12 are a truncated version of the full-length regulatory element (See FIG. 1;). Bd-Actin7 TR1, Bd-Actin7 TR2, Bd-Actin7 TR3, Bd-Actin7 TR4, Bd-Actin7 TR5 Bd-Actin7 TR6, Bd-Actin7 TR7, Bd-Actin7 TR8, Bd-Actin7 TR9, Bd-Actin7 TR10, Bd-Actin7 TR11 regulatory elements respectively consist of 821 bp, 514 bp, 431 bp, 283 bp, and 116 bp and contain the 3' end of the full-length promoter (SEQ ID NOs: 6-12, respectively).

Example 2: Expression Analysis of the Bd-Actin7 Regulatory Element

Bd-Actin7 FL was tested in several different vector configurations. It was operably linked to its native first intron (SEQ ID NO: 3). This intron is located ~60 bp downstream from the beginning of the start codon in the Bd-Actin7 coding region and is approximately 90 bp in length. Bd-Actin7 FL was also operably linked to the first intron of the maize alcohol dehydrogenase gene 1 (ADH1 intron1; (SEQ ID NO: 16) and the first introns of Zm-HPLV9 (SEQ ID NO: 14) and ZM-HPLV11 (SEQ ID NO: 15). Reporter sequences for promoter activity included β-glucuronidase (GUS) and a Lepidoptera insecticidal active, Cry1A.88. The introns were included for the purpose of increased expression as it has been shown that in cereal plant cells the expression of transgenes is enhanced by the presence of some 5' proximal introns (See Callis et al. (1987) *Genes and Development* 1:1183-1200; Kyozuka et al. (1990) *Maydica* 35:353-357).

The Ubi-1 promoter and intron from *Zea mays* were operably linked to the GUS gene so that it could be used to compare the expression pattern and expression levels of the Bd-Actin7 regulatory elements. The Ubi-1 promoter is a strong constitutive promoter in most tissues of *Zea mays*.

Stable transformed plants were created using *Agrobacterium* protocols (See Example 3) to allow for the characterization of promoter activity, including spatial and quantitative expression directed by the Bd-Actin7 FL regulatory element. Plants grown to V5/6 stage under greenhouse conditions were sampled for leaf and root material to evaluate expression changes via histochemical GUS staining analysis and quantitative fluorometric assays. Vegetative growth stages were determined by the number of collared leaves on the plant. Therefore, a plant at V5 stage has 5 fully collared leaves. The plants were then allowed to grow to R1-R2 stage, a point when silks emerge outside the husk (R1 and just start to dry out (R2). Tissues, that included reproductive tissues, were collected and analyzed for expression (Table 2).

TABLE 2

Plant Expression Results for the Bd-Actin7 Promoter (with Bd-Actin7 intron1 and GUS)

| | V5-V6 | | R1-R2 | | |
|---|---|---|---|---|---|
| | Leaf | Root | Stalk | Tassel | Silk | Pollen |
| Bd-Actin 7 FL | 1 | 2 | 2 | 2 | 1 | <0.1 |
| Ubi-1 | 4 | 4 | 4 | 4 | 3 | 4 |
| untransformed (negative control) | 0 | 0 | 0 | 0 | 0 | 0 |

Data shown on a 0-6 scale with maize Ubi-1 promoter directed expression as a comparator.

In another set of experiments, the Bd-Actin7 FL (SEQ ID NO: 1) regulatory element was operably linked to 4 different introns (Bd-Actin7 intron1, ADH intron1 (SEQ ID NO: 16), Zm-HPLV9 (SEQ ID NO: 14) intron1 and Zm-HPSV11 intron1 (SEQ ID NO: 15)) and GUS to test the effect of the introns on expression. Stable transformed plants were created using *Agrobacterium* protocols (See Example 3) and allowed to grow to vegetative (V5/V6) and reproductive (R1/R2) stages when tissues were sampled (Table 3).

TABLE 3

Plant Expression Results for the Bd-Actin7 Promoter and 4 Different Introns

| | V5-V6 | | R1-R2 | | |
|---|---|---|---|---|---|
| | Leaf | Root | Stalk | Husk | Silk | Pollen |
| No intron | 2 | 2 | 2 | 4 | 2 | <0.1 |
| Bd-Actin7 intron1 | 3 | 1 | 3 | 4 | 1 | <0.1 |
| ADH intron1 | 3 | 3 | 3 | 4 | 2 | n.d. |
| Zm-HPLV9 intron1 | 4 | 5 | 5 | 6 | 3 | n.d. |
| Zm-HPSV11 intron1 | 4 | 3 | 3 | 5 | 2 | n.d. |
| untransformed (negative control) | 0 | 0 | 0 | 0 | 0 | 0 |

Data is expressed on a 0-6 scale.

Results from enzyme-linked immunosorbent assays (ELISA) against Cry1A.88 showed the Bd-Actin7 FL regulatory element (SEQ ID NO: 1) directed expression in maize leaf, stalk, and kernel tissues with this reporter (Table 4).

TABLE 4

Plant Expression Results for the Bd-Actin7 FL Regulatory element (with Cry1A.88)

| | V5-V6 | R1-R2 | | Maturity |
|---|---|---|---|---|
| | Leaf | Stalk | Pollen | Kernels |
| No intron | 1 | 2 | <0.1 | 1 |
| Bd-Actin7 intron1 | 1 | 2 | <0.1 | 1 |
| ADH intron1 | 0 | 1 | <0.1 | 0 |
| Zm-HPLV9 intron1 | 1 | 2 | <0.1 | 1 |

TABLE 4-continued

Plant Expression Results for the
Bd-Actin7 FL Regulatory element (with Cry1A.88)

| | V5-V6 | R1-R2 | | Maturity |
|---|---|---|---|---|
| | Leaf | Stalk | Pollen | Kernels |
| Zm-HPSV11 intron1 | 1 | 1 | <0.1 | 1 |
| Ubi-1 | 4 | 5 | 3 | 4 |
| untransformed (negative control) | 0 | 0 | 0 | 0 |

Data is shown on a 0-6 scale with maize Ubi-1 promoter directed expression as a comparator.

Exposing plant tissues to insects provided an assessment of protein expression, as sufficient levels are needed to protect the tissue from the insects. Insufficient expression resulted in feeding damage. Table 5 shows feeding damage of plants transformed with Bd-Actin7 FL (SEQ ID NO: 1) with different introns to plants transformed with Ubi-1 operationally fused to Cry1A.88.

TABLE 5

Corn Earworm Feeding Damage on Ears

| | Median ear feeding damage (cm2) |
|---|---|
| No intron | 2 |
| Bd-Actin7 intron1 | 1 |
| ADH intron1 | 7 |
| Zm-HPLV9 intron1 | 2 |
| Zm-HPSV11 intron1 | 4 |
| Ubi-1 | 1 |
| untransformed (negative control) | >10 |

Three copies of the *Mirabilis* Mosaic Virus transcriptional enhancer (SEQ ID NO: 13) were placed upstream of the Bd-Actin7 FL promoter. In one expression vector the native Bd-Actin 7 intron, Bd-Actin7 intron1 (SEQ ID NO: 3), was present and in another expression vector the intron was absent. Results from transgenic corn plants are shown in Table 6.

TABLE 6

Plant Expression Results for the Bd-Actin7 Promoter
with the 3xMMV Transcriptional Enhancer

| | V5-V6 | | R1-R2 | | | |
|---|---|---|---|---|---|---|
| | Leaf | Root | Stalk | Husk | Silk | Pollen |
| No enhancer/ no intron | 2 | 2 | 2 | 4 | 2 | <0.1 |
| 3xMMV/ no intron | >6 | >6 | >6 | >6 | >6 | <0.1 |
| 3xMMV/ Bd-Actin7 intron1 | >6 | >6 | >6 | >6 | >6 | <0.1 |
| untransformed (negative control) | 0 | 0 | 0 | 0 | 0 | 0 |

Data is shown on a 0-6 scale.

Regulatory elements are a collection of sequence motifs that work together to bind transcription factors that result in the spatial, temporal, and quantitative expression characteristics of a promoter. Understanding the architecture and the positioning of these motifs enhances knowledge pertaining to the regulatory element. Segmental deletion analysis is an important tool that was used to begin to identify regions of the regulatory element that contain functionally important motifs. The removal of segments from the 5' end may change the spatial, temporal, and/or quantitative expression patterns directed by the regulatory element. The regions that result in a change may then be studied more closely to evaluate the sequences and their interaction with cis and trans factors. The truncations may also identify a minimal functional sequence.

Restriction endonuclease recognition sites were used to remove 5' sequence regions from Bd-Actin7 FL ranging in size from ~265 bp to ~693 bp. Each deletion fragment was operably linked to the GUS reporter gene in an expression vector to test in corn plants for expression characteristics relative to the full-length (promoter See Table 7).

TABLE 7

Segmental Deletion Analysis

| | V5-V6 | | | R1-R2 | |
|---|---|---|---|---|---|
| | Leaf | Root | Stalk | Silk | Husk |
| Bd-Actin7 FL | 100 | 100 | 100 | 100 | 100 |
| Bd-Actin7 TR1 | 93 | 77 | 95 | 100 | 98 |
| Bd-Actin7 TR2 | 102 | 87 | 99 | 109 | 101 |
| Bd-Actin7 TR3 | 47 | 27 | 66 | 89 | 66 |
| Bd-Actin7 TR4 | 50 | 30 | 74 | 79 | 89 |
| Bd-Actin7 TR5 | na | na | 69 | 76 | 122 |
| Bd-Actin7 TR6 | na | na | 0 | 0 | 0 |
| untransformed (negative control) | 0 | 0 | 0 | 0 | 0 |

*Data shown as a percentage of the median expression value of Bd-Actin7 FL events Example 3: *Agrobacterium*-Mediated Transformation of Maize and Regeneration of Transgenic Plants For *Agrobacterium*-mediated transformation of maize with a regulatory element sequence of the disclosure, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium* under conditions whereby the bacteria were capable of transferring the regulatory element sequence of the disclosure to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following the co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). Next, inoculated embryos were cultured on medium containing a selective agent and growing transformed calli were recovered (step 4: the selection step). Plantlets were regenerated from the calli (step 5: the regeneration step) prior to transfer to the greenhouse.

What is claimed is:

1. A DNA construct comprising a heterologous transcribable polynucleotide molecule operably linked to the regulatory element polynucleotide, wherein the regulatory element polynucleotide comprises:
   a. a polynucleotide having at least 99% sequence identity to the nucleic acid sequence of any one of SEQ ID NO: 1 or 5-9;
   b. a polynucleotide of any one of SEQ ID NO: 1 or 5-9; or
   c. a functional fragment of at least 100 contiguous nucleotides of any one of SEQ ID NO: 1 or 5-9;
   wherein the regulatory element polynucleotide has promoter activity.

2. The DNA construct of claim 1, wherein the DNA construct further comprises an enhancer regulatory element.

3. The DNA construct of claim 2, wherein enhancer regulatory element comprises SEQ ID NO: 13.

4. The DNA construct of claim 1, wherein the heterologous transcribable polynucleotide molecule is a gene of agronomic interest.

5. The DNA construct of claim 4, wherein the heterologous transcribable polynucleotide molecule is a gene capable of providing herbicide resistance in plants.

6. The DNA construct of claim 4, wherein the heterologous transcribable polynucleotide molecule is a gene capable of providing plant pest control in plants.

7. A heterologous cell stably transformed with the DNA construct of claim 1.

8. A transgenic plant or plant cell stably transformed with the DNA construct of claim 1.

9. The transgenic plant or plant cell of claim 8, wherein the transgenic plant is a dicotyledon plant cell.

10. The transgenic plant or plant cell of claim 8, wherein the transgenic plant is a monocotyledon plant cell.

11. A seed of the transgenic plant of claim 8, wherein the seed comprises the DNA construct.

12. A method for expressing a polynucleotide in a plant comprising introducing into a plant cell a recombinant polynucleotide, said recombinant polynucleotide comprising a regulatory element capable of increasing expression of a heterologous polynucleotide, wherein said regulatory element comprises:
   a. a nucleotide sequence of any one of SEQ ID NO: 1 or 5-9; or
   b. a sequence that is at least 99% identical to any one of SEQ ID NO: 1 or 5-9; or
   c. a nucleotide sequence comprising a functional fragment of at least 100 contiguous nucleotides of any one of SEQ ID NO: 1 or 5-9;
   wherein the nucleotide sequence initiates transcription in a plant cell.

13. The method of claim 12, wherein the heterologous polynucleotide encodes a gene product that is involved in organ development, stem cell development, cell growth stimulation, organogenesis, somatic embryogenesis initiation and development of the apical meristem.

14. The method of claim 12, wherein said heterologous polynucleotide is an endogenous gene of the plant.

15. The method of claim 12, wherein the heterologous polynucleotide encodes a gene product that confers drought tolerance, cold tolerance, herbicide tolerance, pathogen resistance, or insect resistance.

16. The method of claim 12, wherein said plant is a dicot.

17. The method of claim 12, wherein said plant is a monocot.

* * * * *

SEQUENCE LISTING

<160> NUMBER OF SEQ ID NOS: 16

<210> SEQ ID NO 1
<211> LENGTH: 3122
<212> TYPE: DNA
<213> ORGANISM: Brachypodium distachyon

<400> SEQUENCE: 1

| | | | | | |
|---|---|---|---|---|---|
| caagttatgt | tgttgtcatt | ttcacaaata | tgaatttta | cgtgcacgtg | tttaagagac | 60 |
| cgtgacaacg | cacggacgtt | gtactattta | ctttatagaa | gaaagaccgc | gcacgggagg | 120 |
| agatcgacaa | cctcgtgacg | gagtatgcga | tccatcgaat | aaaactcaag | ctctccttaa | 180 |
| tttctcgtgc | catgcgatcc | acggaacgga | cctccaaggc | tccaaaataa | atgacgaatc | 240 |
| tttcgtgcta | cgtgcatgca | catgggcaga | tcagatcaga | tggactaatg | acctgggatt | 300 |
| aattagttaa | ttaatcaatt | tgagagagtc | taatgatcgt | cccgacaccg | tgggcgtggg | 360 |
| ggactgtcga | tagccacgac | aacacgagat | ccataccacg | agaagcagcc | acgtgcacgt | 420 |
| gtgcatcacg | ccaacccaac | catgtttcac | gcaatcatgt | tttcaggcta | gttttaggaa | 480 |
| acttttagaa | cttgtttgat | tattgacatt | cctttctctc | ttttttctac | gcaggttgga | 540 |
| tacacttgga | atcagtttaa | aaataaataa | agggtgcgtt | gtttctcagt | tgcctaattt | 600 |
| gcaagaaaat | agtgttttaa | atctaagttg | gcgaaataga | ttgttgagat | tcgttcgatt | 660 |
| aatatacgag | ggccatccgt | actttcccct | cttccacatc | attagattaa | gttctgacga | 720 |
| ccgagtacgt | caactgattt | ctaactaaaa | ctcagttaag | tttttaaata | gcaaaaccga | 780 |
| aaataaaact | cttgtgatcg | tgcattcgcg | tgcatagaaa | tatgctctca | ggcgctttta | 840 |
| tttttgcaag | gtaggctcta | ttcacgttca | gatgaaaaat | aattaattgt | caaagtacgt | 900 |
| taccttttta | agatcccaac | aatcaacacg | acacaaggct | cgagagatcg | atggtattgg | 960 |
| ctcaagtctt | cgaactttgg | agatttgtat | tgtatattct | tgtaaatttg | atataaaatc | 1020 |
| tgtaatccat | cgaccagtcc | agccttgagc | tgagtttttt | tttttttgga | aagggggcctt | 1080 |
| gagctgagtt | agaaactcat | cgtgcaaagg | accaagttgc | cgttacatta | ctcaatcaga | 1140 |
| gacgcttcaa | agtcacacgc | gcagacgcgc | tgtctccttt | cccatttatt | attttttctgg | 1200 |
| aaaaaaagat | tcagctacaa | gctggatatt | attattttct | aaatcgaaag | ctaattttt | 1260 |
| tataaagaaa | ccgacggaat | attattaggt | gagctgggcc | ttcccctcca | gttggcccag | 1320 |
| gcccaaccag | atcccagcga | agagcgagct | ggaccacttt | acgattcgtg | cagcgcacat | 1380 |
| ccgacgactc | cggacccctc | cacgtcgctc | gtcgtgcggt | ccacgctctc | tatcccccgc | 1440 |
| cagctcattc | cagcctcagg | atctttaaaa | acagattcct | cccttattt | atctcagctg | 1500 |
| tttttttcct | gaacaacttg | tatttttcgc | ggaaggaatt | aaattgcgtt | ttaaaaactg | 1560 |
| gagttttctt | tataggaaaa | taagacagtt | ggtgctattg | tctctttgcc | ccctgctctt | 1620 |
| gtatgaattt | gcaggtgatg | cttttgctac | gcctctctca | taactggttt | ctggtctgtg | 1680 |
| acaactggag | ctgagcaaat | aatttgccca | tcgggggaga | ttcatacctg | gctgtgagat | 1740 |
| gtcactaggc | cctctcttga | aattatttct | gttacaacaa | taatttgatt | cgagccattt | 1800 |
| ctttctttaa | aatggcgtcg | actaaaatag | ttgtgcatga | taggtcaaat | aatttctcga | 1860 |
| tacatcctcg | caaaaaaaaa | tcccaatgct | gcgttgtaga | cattaataaa | agaaaatgca | 1920 |
| tagcatagag | tagaagaaga | aaatttgtta | ctcatttcag | tacttttggt | ataatttgtg | 1980 |
| tttagatcca | tagttcatca | caacacaatt | tccacggttt | ctctatccta | gttttctctt | 2040 |
| gcataccctat | gtttcaaaca | ggtccaagtc | catgtttccc | gaacatcgtt | tggttacgag | 2100 |

```
tatctttctt agatagtctc caattcaaat aattggtccg aaattaaaat ggaaggtttt    2160
aaacagaata cacccatcta tttctctttc cccattttt tttgattttc cagcaaaact    2220
gagaccccat ctatttctct ctttcgtgaa aaggaaaaat aaatcaagtc aggatagaaa    2280
agaaaatccg gggctccata taaaagaggg cacaaggcca agcctagcac ttggctctcc    2340
tgcctctgcc ttagctcttc ctccgccacc accgccgcca cccacccgtc tcctcctctt    2400
cctccgctct ccgctctccg ctcttatcgg cgggaggtct tcaggcgggc aggttcccct    2460
agatcccagg gtaagcgcct ccgtaccagt ccgcgccttc tcttcccctg attcgtcgcg    2520
ctaaatttgg ccgtggaacc cgtgtttttc tcaccgcgag tagtttgttc gtggttcgac    2580
cctgacggtt tctctcgaga accgtagatc cggctcacgg gcgtggtaga actgaacggg    2640
ttgtccggga atctgaaaac cccgtctaat cctttgctgt gtcatttttt tgttctctcg    2700
gtgtatgggt ttacgagttc ggacttggaa ctgatggact ttgatgtggg gtttagattg    2760
tgttggactg gagtagagga gaacggccta tgggtaggtc gtaggttcag tggacgtgtt    2820
agtgttcttg atcagaatga tgattcggtc gtcgattgat tcgttgatgg gtttacttgc    2880
ttattttgta aatcatcatg gagtataaat ttgctagtat tatggaaatg gaagaacaca    2940
aaaagagaga gtagagttac agcatgtaca gataatgtag cctgtagagt ctagatggta    3000
aacattgttg ctgcgctgta gtaaggttga gatttaccat tgtggattat ttatgtattt    3060
tgtgttggga tctgctaata atagccttcc tgtgaaattt gtgcaacaga gtcacttatc    3120
aa                                                                  3122
```

<210> SEQ ID NO 2
<211> LENGTH: 2332
<212> TYPE: DNA
<213> ORGANISM: Brachypodium distachyon

<400> SEQUENCE: 2

```
caagttatgt tgttgtcatt ttcacaaata tgaatttta cgtgcacgtg tttaagagac      60
cgtgacaacg cacggacgtt gtactattta ctttatagaa gaaagaccgc gcacgggagg    120
agatcgacaa cctcgtgacg gagtatgcga tccatcgaat aaaactcaag ctctccttaa    180
tttctcgtgc catgcgatcc acggaacgga cctccaaggc tccaaaataa atgacgaatc    240
tttcgtgcta cgtgcatgca catgggcaga tcagatcaga tggactaatg acctgggatt    300
aattagttaa ttaatcaatt tgagagagtc taatgatcgt cccgacaccg tgggcgtggg    360
ggactgtcga tagccacgac aacacgagat ccataccacg agaagcagcc acgtgcacgt    420
gtgcatcacg ccaacccaac catgtttcac gcaatcatgt tttcaggcta gttttaggaa    480
acttttagaa cttgttgat tattgacatt cctttctctc ttttttctac gcaggttgga    540
tacacttgga atcagtttaa aaataaataa agggtgcgtt gtttctcagt tgcctaattt    600
gcaagaaaat agtgttttaa atctaagttg gcgaaataga ttgttgagat tcgttcgatt    660
aatatacgag ggccatccgt actttccct cttccacatc attagattaa gttctgacga    720
ccgagtacgt caactgattt ctaactaaaa ctcagttaag ttttaaata gcaaaaccga    780 aaataaaact cttgtgatcg tgcattcgcg tgcatagaaa tatgctctca ggcgcttta    840 ttttgcaag gtaggctcta ttcacgttca gatgaaaaat aattaattgt caaagtacgt    900
taccttttta agatcccaac aatcaacacg acacaaggct cgagagatcg atggtattgg    960
ctcaagtctt cgaactttgg agatttgtat tgtatattct tgtaaatttg atataaaatc   1020
```

```
tgtaatccat cgaccagtcc agccttgagc tgagtttttt ttttttttgga aaggggcctt    1080 gagctgagtt agaaactcat cgtgcaaagg accaagttgc cgttacatta ctcaatcaga    1140
gacgcttcaa agtcacacgc gcagacgcgc tgtctccttt cccatttatt attttttctgg   1200 aaaaaaagat tcagctacaa gctggatatt attattttct aaatcgaaag ctaattttt     1260 tataaagaaa ccgacggaat attattaggt gagctgggcc ttcccctcca gttggcccag    1320
gcccaaccag atcccagcga agagcgagct ggaccacttt acgattcgtg cagcgcacat    1380
ccgacgactc cggacccctc cacgtcgctc gtcgtgcggt ccacgctctc tatcccccgc    1440
cagctcattc cagcctcagg atctttaaaa acagattcct cccctttatt atctcagctg    1500 ttttttttcct gaacaacttg tattttttcgc ggaaggaatt aaattgcgtt ttaaaaactg  1560
gagttttctt tataggaaaa taagacagtt ggtgctattg tctctttgcc ccctgctctt    1620
gtatgaattt gcaggtgatg cttttgctac gcctctctca taactggttt ctggtctgtg    1680
acaactggag ctgagcaaat aatttgccca tcgggggaga ttcatacctg gctgtgagat    1740
gtcactaggc cctctcttga aattattttct gttacaacaa taatttgatt cgagccattt    1800 cttttctttaa aatggcgtcg actaaaatag ttgtgcatga taggtcaaat aatttctcga   1860
tacatcctcg caaaaaaaaa tcccaatgct gcgttgtaga cattaataaa agaaaatgca    1920
tagcatagag tagaagaaga aaatttgtta ctcatttcag tacttttggt ataatttgtg    1980
tttagatcca tagttcatca caacacaatt tccacggttt ctctatccta gttttctctt    2040
gcatacctat gtttcaaaca ggtccaagtc catgtttccc gaacatcgtt tggttacgag    2100
tatctttctt agatagtctc caattcaaat aattggtccg aaattaaaat ggaaggtttt    2160
aaacagaata cacccatcta tttctctttc cccatttttt tttgattttc cagcaaaact    2220
gagaccccat ctatttctct ctttcgtgaa aaggaaaaat aaatcaagtc aggatagaaa    2280
agaaaatccg gggctccata taaagaggg cacaaggcca agcctagcac tt             2332

<210> SEQ ID NO 3
<211> LENGTH: 639
<212> TYPE: DNA
<213> ORGANISM: Brachypodium distachyon

<400> SEQUENCE: 3
gtaagcgcct ccgtaccagt ccgcgccttc tcttcccctg attcgtcgcg ctaaatttgg      60
ccgtggaacc cgtgttttc tcaccgcgag tagtttgttc gtggttcgac cctgacggtt     120
tctctcgaga accgtagatc cggctcacgg gcgtggtaga actgaacggg ttgtccggga    180
atctgaaaac cccgtctaat cctttgctgt gtcattttt tgttctctcg gtgtatgggt     240
ttacgagttc ggacttggaa ctgatggact ttgatgtggg gtttagattg tgttggactg    300
gagtagagga gaacggccta tgggtaggtc gtaggttcag tggacgtgtt agtgttcttg    360
atcagaatga tgattcggtc gtcgattgat tcgttgatgg gtttacttgc ttattttgta    420
aatcatcatg gagtataaat ttgctagtat tatggaaatg gaagaacaca aaaagagaga    480
gtagagttac agcatgtaca gataatgtag cctgtagagt ctagatggta aacattgttg    540
ctgcgctgta gtaaggttga gatttaccat tgtggattat ttatgtattt tgtgttggga    600
tctgctaata atagccttcc tgtgaaattt gtgcaacag                            639

<210> SEQ ID NO 4
<211> LENGTH: 90
<212> TYPE: DNA
<213> ORGANISM: Brachypodium distachyon
```

```
<400> SEQUENCE: 4
gttcgtatgt ctccttctga atgagtgata taaattcttg ttatggttta catggtactg    60
aatttagatg gtgttctgta ttctctgcag                                     90

<210> SEQ ID NO 5
<211> LENGTH: 2810
<212> TYPE: DNA
<213> ORGANISM: Brachypodium distachyon

<400> SEQUENCE: 5
aatcaatttg agagagtcta atgatcgtcc cgacaccgtg ggcgtggggg actgtcgata    60
gccacgacaa cacgagatcc ataccacgag aagcagccac gtgcacgtgt gcatcacgcc   120
aacccaacca tgtttcacgc aatcatgttt tcaggctagt tttaggaaac ttttagaact   180
tgtttgatta ttgacattcc tttctctctt ttttctacgc aggttggata cacttggaat   240
cagtttaaaa ataaataaag ggtgcgttgt ttctcagttg cctaatttgc aagaaaatag   300
tgttttaaat ctaagttggc gaaatagatt gttgagattc gttcgattaa tatacgaggg   360
ccatccgtac tttcccctct tccacatcat tagattaagt tctgacgacc gagtacgtca   420
actgatttct aactaaaact cagttaagtt tttaaatagc aaaaccgaaa ataaaactct   480
tgtgatcgtg cattcgcgtg catagaaata tgctctcagg cgcttttatt tttgcaaggt   540
aggctctatt cacgttcaga tgaaaaataa ttaattgtca aagtacgtta cctttttaag   600
atcccaacaa tcaacacgac acaaggctcg agagatcgat ggtattggct caagtcttcg   660
aactttggag atttgtattg tatattcttg taaatttgat ataaaatctg taatccatcg   720
accagtccag ccttgagctg agtttttttt tttttggaaa ggggccttga gctgagttag   780
aaactcatcg tgcaaaggac caagttgccg ttacattact caatcagaga cgcttcaaag   840
tcacacgcgc agacgcgctg tctcctttcc catttattat ttttctggaa aaaaagattc   900
agctacaagc tggatattat tattttctaa atcgaaagct aattttttta taagaaaacc   960
gacggaatat tattaggtga gctgggcctt cccctccagt tggcccaggc ccaaccagat  1020
cccagcgaag agcgagctgg accactttac gattcgtgca gcgcacatcc gacgactccg  1080 gaccccctcca cgtcgctcgt cgtgcggtcc acgctctcta tccccgcca gctcattcca  1140 gcctcaggat ctttaaaaac agattcctcc ccttatttat ctcagctgtt ttttttcctga  1200 acaacttgta ttttcgcgg aaggaattaa attgcgtttt aaaaactgga gttttcttta  1260
taggaaaata agacagttgg tgctattgtc tctttgcccc ctgctcttgt atgaatttgc  1320
aggtgatgct tttgctacgc ctctctcata actggtttct ggtctgtgac aactggagct  1380
gagcaaaata tttgcccatc gggggagatt catacctggc tgtgagatgt cactaggccc  1440
tctcttgaaa ttatttctgt tacaacaata atttgattcg agccatttct ttctttaaaa  1500
tggcgtcgac taaaatagtt gtgcatgata ggtcaaataa tttctcgata catcctcgca  1560
aaaaaaaatc ccaatgctgc gttgtagaca ttaataaaag aaaatgcata gcatagagta  1620
gaagaagaaa atttgttact catttcagta cttttggtat aatttgtgtt tagatccata  1680
gttcatcaca acacaatttc cacggtttct ctatcctagt ttttctttgc ataccctatgt  1740 ttcaaacagg tccaagtcca tgtttcccga acatcgtttg gttacgagta tctttcttag  1800
atagtctcca attcaaataa ttggtccgaa attaaaatgg aaggttttaa acagaataca  1860
cccatctatt tctcttccc cattttttttt tgattttcca gcaaaactga gaccccatct  1920
```

```
atttctctct ttcgtgaaaa ggaaaaataa atcaagtcag gatagaaaag aaaatccggg    1980
gctccatata aaagagggca caaggccaag cctagcactt ggctctcctg cctctgcctt    2040
agctcttgct ccgccaccac cgccgccacc cacccgtctc ctcctcttcc tccgctctcc    2100
gctctccgct cttatcggcg ggaggtcttc aggcgggcag gttcccctag atcccagggt    2160
aagcgcctcc gtaccagtcc gcgccttctc ttcccctgat tcgtcgcgct aaatttggcc    2220
gtggaacccg tgttttctc accgcgagta gtttgttcgt ggttcgaccc tgacggtttc    2280
tctcgagaac cgtagatccg gctcacgggc gtggtagaac tgaacgggtt gtccgggaat    2340
ctgaaaaccc cgtctaatcc tttgctgtgt cattttttg ttctctcggt gtatgggttt    2400
acgagttcgg acttggaact gatggacttt gatgtggggt ttagattgtg ttggactgga    2460
gtagaggaga acggcctatg ggtaggtcgt aggttcagtg gacgtgttag tgttcttgat    2520
cagaatgatg attcggtcgt cgattgattc gttgatgggt ttacttgctt attttgtaaa    2580
tcatcatgga gtataaattt gctagtatta tggaaatgga agaacacaaa aagagagagt    2640
agagttacag catgtacaga taatgtagcc tgtagagtct agatggtaaa cattgttgct    2700
gcgctgtagt aaggttgaga tttaccattg tggattattt atgtattttg tgttgggatc    2760
tgctaataat agccttcctg tgaaatttgt gcaacagagt cacttatcaa                2810

<210> SEQ ID NO 6
<211> LENGTH: 2174
<212> TYPE: DNA
<213> ORGANISM: Brachypodium distachyon

<400> SEQUENCE: 6
cgatggtatt ggctcaagtc ttcgaacttt ggagatttgt attgtatatt cttgtaaatt      60
tgatataaaa tctgtaatcc atcgaccagt ccagccttga gctgagtttt ttttttttg     120 gaaagggcc ttgagctgag ttagaaactc atcgtgcaaa ggaccaagtt gccgttacat     180
tactcaatca gagacgcttc aaagtcacac gcgcagacgc gctgtctcct ttcccattta     240
ttatttttct ggaaaaaaag attcagctac aagctggata ttattatttt ctaaatcgaa     300
agctaatttt tttataaaga aaccgacgga atattattag gtgagctggg ccttcccctc     360
cagttggccc aggcccaacc agatcccagc gaagagcgag ctggaccact ttacgattcg     420
tgcagcgcac atccgacgac tccggacccc tccacgtcgc tcgtcgtgcg gtccacgctc     480
tctatccccc gccagctcat tccagcctca ggatctttaa aaacagattc ctccccttat     540
ttatctcagc tgttttttc ctgaacaact tgtattttc gcggaaggaa ttaaattgcg     600
ttttaaaaac tggagttttc tttataggaa aataagacag ttggtgctat tgtctctttg     660 cccctgctc ttgtatgaat ttgcaggtga tgcttttgct acgcctctct cataactggt     720
ttctggtctg tgacaactgg agctgagcaa ataatttgcc catcggggga gattcatacc     780
tggctgtgag atgtcactag gccctctctt gaaattattt ctgttacaac aataatttga     840
ttcgagccat ttctttcttt aaaatggcgt cgactaaaat agttgtgcat gataggtcaa     900
ataatttctc gatacatcct cgcaaaaaaa aatcccaatg ctgcgttgta gacattaata     960
aaagaaaatg catagcatag agtagaagaa gaaaatttgt tactcatttc agtacttttg    1020
gtataatttg tgtttagatc catagttcat cacaacacaa tttccacggt ttctctatcc    1080 tagttttct ttgcataccct atgtttcaaa caggtccaag tccatgtttc ccgaacatcg    1140
tttggttacg agtatctttc ttagatagtc tccaattcaa ataattggtc cgaaattaaa    1200
atggaaggtt ttaaacagaa tacacccatc tatttctctt tccccatttt tttttgattt    1260
```

```
tccagcaaaa ctgagacccc atctatttct ctctttcgtg aaaaggaaaa ataaatcaag    1320
tcaggataga aaagaaaatc cggggctcca tataaaagag ggcacaaggc caagcctagc    1380
acttggctct cctgcctctg ccttagctct tgctccgcca ccaccgccgc cacccacccg    1440
tctcctcctc ttcctccgct ctccgctctc cgctcttatc ggcgggaggt cttcaggcgg    1500
gcaggttccc ctagatccca gggtaagcgc ctccgtacca gtccgcgcct tctcttcccc    1560
tgattcgtcg cgctaaattt ggccgtggaa cccgtgtttt tctcaccgcg agtagtttgt    1620
tcgtggttcg accctgacgg tttctctcga aaccgtaga tccggctcac gggcgtggta    1680
gaactgaacg ggttgtccgg gaatctgaaa accccgtcta atcctttgct gtgtcatttt    1740
tttgttctct cggtgtatgg gtttacgagt tcggacttgg aactgatgga ctttgatgtg    1800
gggtttagat tgtgttggac tggagtagag gagaacggcc tatgggtagg tcgtaggttc    1860
agtggacgtg ttagtgttct tgatcagaat gatgattcgg tcgtcgattg attcgttgat    1920
gggtttactt gcttattttg taaatcatca tggagtataa atttgctagt attatggaaa    1980
tggaagaaca caaaagaga gagtagagtt acagcatgta cagataatgt agcctgtaga    2040
gtctagatgg taaacattgt tgctgcgctg tagtaaggtt gagatttacc attgtggatt    2100
atttatgtat tttgtgttgg gatctgctaa taatagcctt cctgtgaaat tgtgcaaca    2160 gagtcactta tcaa                                                      2174

<210> SEQ ID NO 7
<211> LENGTH: 1666
<212> TYPE: DNA
<213> ORGANISM: Brachypodium distachyon

<400> SEQUENCE: 7
caggatcttt aaaaacagat tcctcccctt atttatctca gctgtttttt tcctgaacaa      60
cttgtatttt tcgcggaagg aattaaattg cgttttaaaa actggagttt tctttatagg     120
aaaataagac agttggtgct attgtctctt tgcccctgc tcttgtatga atttgcaggt     180
gatgcttttg ctacgcctct ctcataactg gtttctggtc tgtgacaact ggagctgagc     240
aaataatttg cccatcgggg gagattcata cctggctgtg agatgtcact aggccctctc     300
ttgaaattat ttctgttaca acaataattt gattcgagcc atttctttct ttaaaatggc     360
gtcgactaaa atagttgtgc atgataggtc aaataatttc tcgatacatc ctcgcaaaaa     420
aaaatcccaa tgctgcgttg tagacattaa taaagaaaa tgcatagcat agagtagaag     480
aagaaaattt gttactcatt tcagtacttt tggtataatt tgtgtttaga tccatagttc     540
atcacaacac aatttccacg gtttctctat cctagttttt ctttgcatac ctatgtttca     600
aacaggtcca agtccatgtt tcccgaacat cgtttggtta cgagtatctt tcttagatag     660
tctccaattc aaataattgg tccgaaatta aaatggaagg ttttaaacag aatacaccca     720
tctatttctc tttccccatt tttttttgat tttccagcaa aactgagacc ccatctattt     780
ctctctttcg tgaaaaggaa aaataaatca agtcaggata gaaaagaaaa tccggggctc     840
catataaaag agggcacaag gccaagccta gcacttggct ctcctgcctc tgccttagct     900
cttgctccgc caccaccgcc gccacccacc cgtctcctcc tcttcctccg ctctccgctc     960
tccgctctta tcggcgggag gtcttcaggc gggcaggttc ccctagatcc cagggtaagc    1020
gcctccgtac cagtccgcgc cttctcttcc cctgattcgt cgcgctaaat ttggccgtgg    1080
aacccgtgtt tttctcaccg cgagtagttt gttcgtggtt cgaccctgac ggtttctctc    1140
```

| | |
|---|---:|
| gagaaccgta gatccggctc acgggcgtgg tagaactgaa cgggttgtcc gggaatctga | 1200 |
| aaacccgtc taatcctttg ctgtgtcatt tttttgttct ctcggtgtat gggtttacga | 1260 |
| gttcggactt ggaactgatg gactttgatg tggggtttag attgtgttgg actggagtag | 1320 |
| aggagaacgg cctatgggta ggtcgtaggt tcagtggacg tgttagtgtt cttgatcaga | 1380 |
| atgatgattc ggtcgtcgat tgattcgttg atgggtttac ttgcttattt tgtaaatcat | 1440 |
| catggagtat aaatttgcta gtattatgga aatggaagaa cacaaaaaga gagagtagag | 1500 |
| ttacagcatg tacagataat gtagcctgta gagtctagat ggtaaacatt gttgctgcgc | 1560 |
| tgtagtaagg ttgagattta ccattgtgga ttatttatgt attttgtgtt gggatctgct | 1620 |
| aataatagcc ttcctgtgaa atttgtgcaa cagagtcact tatcaa | 1666 |

<210> SEQ ID NO 8
<211> LENGTH: 1161
<212> TYPE: DNA
<213> ORGANISM: Brachypodium distachyon

<400> SEQUENCE: 8

| | |
|---|---:|
| acttttggta taatttgtgt ttagatccat agttcatcac aacacaattt ccacggtttc | 60 |
| tctatcctag ttttttcttt g catacctatg tttcaaacag gtccaagtcc atgtttcccg | 120 |
| aacatcgttt ggttacgagt atctttctta gatagtctcc aattcaaata attggtccga | 180 |
| aattaaaatg gaaggtttta aacagaatac acccatctat ttctctttcc ccattttttt | 240 |
| ttgattttcc agcaaaactg agaccccatc tatttctctc tttcgtgaaa aggaaaaata | 300 |
| aatcaagtca ggatagaaaa gaaatccgg ggctccatat aaaagagggc acaaggccaa | 360 |
| gcctagcact tggctctcct gcctctgcct tagctcttgc tccgccacca ccgccgccac | 420 |
| ccacccgtct cctcctcttc ctccgctctc cgctctccgc tcttatcggc gggaggtctt | 480 |
| caggcgggca ggttcccta gatcccaggg taagcgcctc cgtaccagtc cgcgccttct | 540 |
| cttcccctga ttcgtcgcgc taaatttggc cgtggaaccc cgttttttct caccgcgagt | 600 |
| agtttgttcg tggttcgacc ctgacggttt ctctcgagaa ccgtagatcc ggctcacggg | 660 |
| cgtggtagaa ctgaacgggt tgtccgggaa tctgaaaacc ccgtctaatc ctttgctgtg | 720 |
| tcattttttt gttctctcgg tgtatgggtt tacgagttcg gacttggaac tgatggactt | 780 |
| tgatgtgggg tttagattgt gttggactgg agtagaggag aacggcctat gggtaggtcg | 840 |
| taggttcagt ggacgtgtta gtgttcttga tcagaatgat gattcggtcg tcgattgatt | 900 |
| cgttgatggg tttacttgct tattttgtaa atcatcatgg agtataaatt tgctagtatt | 960 |
| atggaaatgg aagaacacaa aaagagagag tagagttaca gcatgtacag ataatgtagc | 1020 |
| ctgtagagtc tagatggtaa acattgttgc tgcgctgtag taaggttgag atttaccatt | 1080 |
| gtggattatt tatgtatttt gtgttgggat ctgctaataa tagccttcct gtgaaatttg | 1140 |
| tgcaacagag tcacttatca a | 1161 |

<210> SEQ ID NO 9
<211> LENGTH: 528
<212> TYPE: DNA
<213> ORGANISM: Brachypodium distachyon

<400> SEQUENCE: 9

| | |
|---|---:|
| tcgagaaccg tagatccggc tcacgggcgt ggtagaactg aacgggttgt ccgggaatct | 60 |
| gaaaaccccg tctaatcctt tgctgtgtca ttttttttgtt ctctcggtgt atgggtttac | 120 |
| gagttcggac ttggaactga tggactttga tgtggggttt agattgtgtt ggactggagt | 180 |

```
agaggagaac ggcctatggg taggtcgtag gttcagtgga cgtgttagtg ttccttgatca    240 gaatgatgat tcggtcgtcg attgattcgt tgatgggttt acttgcttat tttgtaaatc    300
atcatggagt ataaatttgc tagtattatg gaaatggaag aacacaaaaa gagagagtag    360
agttacagca tgtacagata atgtagcctg tagagtctag atggtaaaca ttgttgctgc    420
gctgtagtaa ggttgagatt taccattgtg gattatttat gtattttgtg ttgggatctg    480
ctaataatag ccttcctgtg aaatttgtgc aacagagtca cttatcaa                 528

<210> SEQ ID NO 10
<211> LENGTH: 528
<212> TYPE: DNA
<213> ORGANISM: Brachypodium distachyon

<400> SEQUENCE: 10
tcgagaaccg tagatccggc tcacgggcgt ggtagaactg aacgggttgt ccgggaatct    60
gaaaaccccg tctaatcctt tgctgtgtca tttttttgtt ctctcggtgt atgggtttac   120
gagttcggac ttgaactga tggactttga tgtggggttt agattgtgtt ggactggagt    180
agaggagaac ggcctatggg taggtcgtag gttcagtgga cgtgttagtg ttccttgatca   240 gaatgatgat tcggtcgtcg attgattcgt tgatgggttt acttgcttat tttgtaaatc    300
atcatggagt ataaatttgc tagtattatg gaaatggaag aacacaaaaa gagagagtag    360
agttacagca tgtacagata atgtagcctg tagagtctag atggtaaaca ttgttgctgc    420
gctgtagtaa ggttgagatt taccattgtg gattatttat gtattttgtg ttgggatctg    480
ctaataatag ccttcctgtg aaatttgtgc aacagagtca cttatcaa                 528

<210> SEQ ID NO 11
<211> LENGTH: 293
<212> TYPE: DNA
<213> ORGANISM: Brachypodium distachyon

<400> SEQUENCE: 11
gatcagaatg atgattcggt cgtcgattga ttcgttgatg ggtttacttg cttattttgt    60
aaatcatcat ggagtataaa tttgctagta ttatggaaat ggaagaacac aaaagagag   120 agtagagtta cagcatgtac agataatgta gcctgtagag tctagatggt aaacattgtt   180
gctgcgctgt agtaaggttg agatttacca ttgtggatta tttatgtatt ttgtgttggg   240
atctgctaat aatagccttc ctgtgaaatt tgtgcaacag agtcacttat caa           293

<210> SEQ ID NO 12
<211> LENGTH: 132
<212> TYPE: DNA
<213> ORGANISM: Brachypodium distachyon

<400> SEQUENCE: 12
ctagatggta aacattgttg ctgcgctgta gtaaggttga gatttaccat tgtggattat    60
ttatgtattt tgtgttggga tctgctaata atagccttcc tgtgaaattt gtgcaacaga   120
gtcacttatc aa                                                        132

<210> SEQ ID NO 13
<211> LENGTH: 573
<212> TYPE: DNA
<213> ORGANISM: Mirabilis Mosaic Virus

<400> SEQUENCE: 13
```

```
ccactaaaac attgctttgt caaaagctaa aaaagatgat gcccgacagc cacttgtgtg    60
aagcatgaga agccggtccc tccactaaga aaattagtga agcatcttcc agtggtccct   120
ccactcacag ctcaatcagt gagcaacagg acgaaggaaa tgacgtaagc catgacgtct   180
aatcccactc gagccactaa acattgctt tgtcaaaagc taaaaagat gatgcccgac     240
agccacttgt gtgaagcatg agaagccggt ccctccacta gaaaattag tgaagcatct    300
tccagtggtc cctccactca cagctcaatc agtgagcaac aggacgaagg aaatgacgta   360
agccatgacg tctaatccca gtcgacccac taaaacattg ctttgtcaaa agctaaaaaa   420
gatgatgccc gacagccact tgtgtgaagc atgagaagcc ggtccctcca ctaagaaaat   480
tagtgaagca tcttccagtg gtccctccac tcacagctca atcagtgagc aacaggacga   540
aggaaatgac gtaagccatg acgtctaatc cca                                573

<210> SEQ ID NO 14
<211> LENGTH: 856
<212> TYPE: DNA
<213> ORGANISM: Zea mays

<400> SEQUENCE: 14
gtaaggttcc cttccctcct cccctcacac ccctgttcgt gttccttcgg atcggatctc    60
agtggtgatg ttagacgtcc gcggctgcct acgtagtggc attgccgccc gaaaggtttg   120
tttaggtggg gtagatccga aacaggccgg atctggacca tgtccgcggc ggggcggcgg   180
gacttgatcg cgtagctgtc gtgtgcattt ctccctacca gtggcggaat cggcgatgtg   240
gacctaaggg ctaaggctta tctgctgcct tgaccatttc gtcgctgaca aaacaaagt    300
gacaatcatg ccgttctctg tttgtttatc tggatcgtta ttacgctgtg aatcctgcga   360
tatgtggcta agtgattttt cttcttttc tgggggcagt ttagcctttg acccagtcct    420
aggtgtggtc actaggactg tgtagcatga tgagtgaggt tgcagcaggc tgattgctag   480
tggacgtttt tttccccaat ttgttaggtt ttcacgctcc aggttgtgca agtaattttg   540
ctagtgattg tgtgatccat cttcaacgtt gaaccttgtt tttcccccta aacccccaa    600
caggaaatct tgccccgact tctattgcaa aaattgtaac gcttagcacc ctgattgact   660
caattcctgt cactaggcat gctcggtcaa aagcagatga tttaccactt agaaactgcc   720
ctgcccctgc tttccacata gcatttcgaa ctttttgact actattgaca ccccctaac    780
ttgccgaact atttctctct tcagctacta tttacctagt tataattaca taaatgtttg   840
tgtgtatctt gtgcag                                                   856

<210> SEQ ID NO 15
<211> LENGTH: 632
<212> TYPE: DNA
<213> ORGANISM: Zea mays

<400> SEQUENCE: 15
gtgaggagcc ttctctctct ctctctctct ttctctgtct ctctctcttc ctaacctttc    60
ttcccttcgt cctcgtcccc cacgctctgc tcttgtggaa ttttctatta gcgtctgccg   120
ccatttgttt cggctacttt gtgcgcgcgc aagcgcaaac cacgggggtc tctctcgtgt   180
tcgccattct gccgaatcgc cactgcaagc tcttctaccg cttctgtgt gctctgacat    240
ctggactccg gagtccggac gtccgcggct ctgtttgctg cgcttgtttt ctttttccca   300
gctatgcttc gtttcttctc gaattccatt ttttatctc tctttttcc ctcgtggacg     360
aagcaaagca agcaagacga ccttgcatct gagactctga gactgtactg tttctttgc    420
```

-continued

```
cattgggttt ttccctaaga ttccttttg gctgccaatg ttcagtccga cagcagcacc    480
cgctgcaacc atttcagcac ttcttccgcc tctgtttcca taatatttct tctttttttt    540
ttccatctct tttttttgt gtgtgctata gcttttgctt gactgaaacg cagcacacac    600
cttacacaac caaacatttt tttttggcgc ag                                   632

<210> SEQ ID NO 16
<211> LENGTH: 538
<212> TYPE: DNA
<213> ORGANISM: Zea mays

<400> SEQUENCE: 16
gtccgccttg tttctcctct gtctcttgat ctgactaatc ttggtttatg attcgttgag     60 taatttggg gaaagcttcg tccacagttt tttttcgat gaacagtgcc gcagtggcgc    120
tgatcttgta tgctatcctg caatcgtggt gaacttattt cttttatatc cttcactccc    180
atgaaaaggc tagtaatctt tctcgatgta acatcgtcca gcactgctat taccgtgtgg    240
tccatccgac agtctggctg aacacatcat acgatattga gcaaagatcg atctatcttc    300
cctgttcttt aatgaaagac gtcattttca tcagtatgat ctaagaatgt tgcaacttgc    360
aaggaggcgt ttctttcttt gaatttaact aactcgttga gtggccctgt ttctcggacg    420
taaggccttt gctgctccac acatgtccat tcgaatttta ccgtgtttag caagggcgaa    480
aagtttgcat cttgatgatt tagcttgact atgcgattgc tttcctggac ccgtgcag     538
```